US00PP26723P3

(12) United States Plant Patent
Schoone

(10) Patent No.: US PP26,723 P3
(45) Date of Patent: May 10, 2016

(54) *PHALAENOPSIS* ORCHID PLANT NAMED 'SNOW VIRGIN'

(50) Latin Name: *Phalaenopsis hybrida*
Varietal Denomination: Snow Virgin

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 223 days.

(21) Appl. No.: 13/999,419

(22) Filed: Feb. 25, 2014

(65) Prior Publication Data

US 2014/0317810 P1 Oct. 23, 2014

Related U.S. Application Data

(60) Provisional application No. 61/814,560, filed on Apr. 22, 2013.

(30) Foreign Application Priority Data

Apr. 25, 2013 (NL) ..... PBR OPS1028

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
CPC ..... A01H 5/02
See application file for complete search history.

*Primary Examiner* — Kent L Bell
(74) *Attorney, Agent, or Firm* — Foley & Lardner LLP; Sunit Talapatra

(57) ABSTRACT

A new and distinct *Phalaenopsis* plant named 'Snow Virgin' particularly characterized by flowers which are white with some green/yellow in the labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Snow Virgin'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Snow Virgin'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Snow Virgin' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Snow Virgin' originated from a cross made by the inventor in 2000 in Strengweg, Heemskerk, The Netherlands. The female or seed parent is the *Phalaenopsis* cultivar designated 'Snow Tiger', unpatented. The male or pollen parent is the *Phalaenopsis* cultivar designated 'Funny Virgin', unpatented. The new *Phalaenopsis* 'Snow Virgin' was discovered and selected by the inventor as a single flowering plant within the progeny of the stated cross in a controlled environment in 2008 in Strengweg, Heemskerk, The Netherlands.

Asexual reproduction of the new *Phalaenopsis* cultivar by tissue culture was first performed in November, 2008 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Snow Virgin', which in combination distinguish this *Phalaenopsis* as a new and distinct cultivar:

1. flowers which are white with some green/yellow in the labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Snow Virgin', the female parent 'Snow Tiger' has white flowers which are about 10 cm in size; the raceme is about 60 cm. The male parent 'Funny Virgin' has white colored flowers which are about 9 cm in size; the raceme is about 70 cm, whereas the flowers of 'Snow Virgin' are white and about 8 cm in size. The raceme is about 60 to 70 cm.

Presently, the commercial cultivar to which 'Snow Virgin' can be meaningfully compared is 'Doremi'. 'Snow Virgin' has a lager raceme than 'Doremi' and 'Snow Virgin' has green/yellow in the labellum, whereas 'Doremi' has yellow in the labellum.

BRIEF DESCRIPTION OF THE PHOTOGRAPHS

The accompanying photographs illustrate the overall appearance of the new *Phalaenopsis* 'Snow Virgin' showing the colors as true as is reasonably possible with colored reproductions of this type. Colors in the photographs may differ slightly from the color values cited in the detailed botanical description, which accurately describe the color of 'Snow Virgin'.

DETAILED BOTANICAL DESCRIPTION

Figure 1:
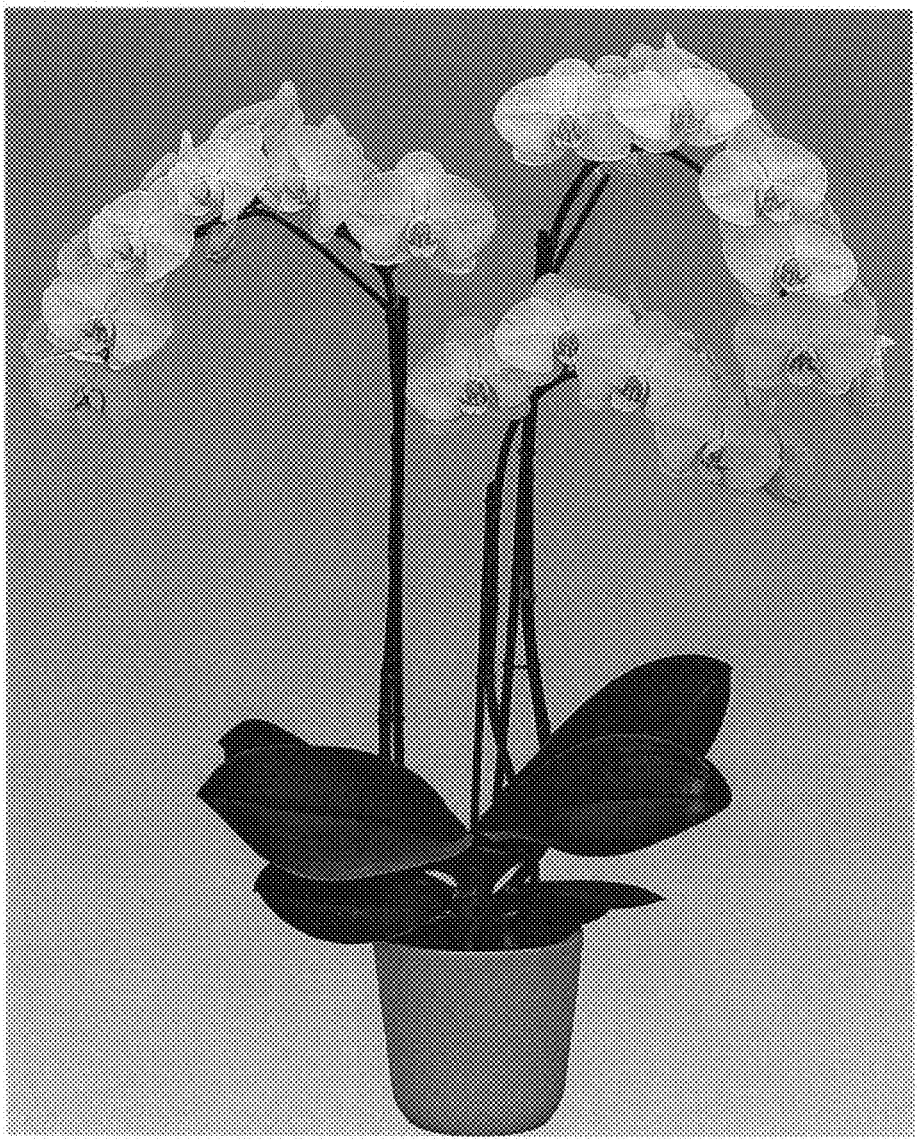
FIG. 1 shows a side view perspective of a typical flowering plant of 'Snow Virgin' in a 12 cm pot, at 16 months of age.

The new *Phalaenopsis* cultivar 'Snow Virgin' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Snow Virgin' as grown in a greenhouse in Strengweg, Heemskerk, The Netherlands, under conditions which closely approximate those generally used in commercial practice. Initially, the ideal temperature to grow plants of 'Snow Virgin' is 27° C. during the day and at night. Then, during the flowering phase of 'Snow Virgin', the ideal growing temperature is 20-22° C. during the day and 18° C. at night. Light levels for growing 'Snow Virgin' are a minimum of 5,000 lux and a maximum of 10,000 lux. A balanced fertilizer with level of 200 ppm N, 87 ppm P, 168 ppm K is applied. Duration of growth of 'Snow Virgin' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Snow Virgin' plants described is 12 months after potting.

Classification:

*Botanical.*—*Phalaenopsis hybrida.*

Parentage:

*Female or seed parent.*—*Phalaenopsis* cultivar designated 'Snow Tiger', unpatented.

*Male or pollen parent.*—*Phalaenopsis* cultivar designated 'Funny Virgin', unpatented.

Propagation:

*Type.*—Tissue culture.

*Rooting habit and description.*—Fleshy; approximately 4 mm-8 mm wide and greyed/green and green in color (RHS 194A and RHS 137B); freely branching. It takes 12 weeks for plants growing in tissue culture to initiate roots.

Plant:

*Size at maturity.*—Height (from bottom of pot to highest flower): about 70-80 cm. Spread: about 50 to 80 cm.

*Growth habit.*—Standard; green leaves (RHS 137B) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19 ° C. about 2 racemes with flowers appear.

Foliage:

*Quantity per plant.*—About 6 to 10 leaves are produced before flowering.

*Arrangement and attachment.*—Half up/horizontal and on two sides.

*Overall shape of leaf.*—Oval, the tip is blunt and asymmetric.

*Texture* (*upper* & *underside*).—Smooth and leathery.

*Pubescence.*—None.

*Mature leaf length.*—About 15 to 25 cm.

*Mature leaf width.*—About 7 to 9 cm.

*Mature leaf thickness.*—About 2 mm.

*Mature leaf color.*—Upper side: green (RHS 137B). Under side: yellow/green (RHS 146B).

*Leaf base.*—Acute.

*Margin.*—Entire.

*Venation.*—Pattern: parallel. Color of midvein: upper side: green (RHS 137B). Under side: yellow/green (RHS 146B).

Raceme:

*Quantity per plant.*—About 1 to 3.

*Number of flowers per raceme.*—About 10 to 22.

*Length.*—About 60 to 70 cm.

*Diameter.*—About 6 mm.

*Strength.*—Strong.

*Aspect.*—Upright.

*Texture.*—Glabrous and smooth.

*Color.*—Green (RHS N137A) with yellow/green (RHS 144C).

*Internode.*—Length: about 40 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 30 mm. Diameter (at midpoint): about 25 mm. Shape: oval with a bump on the side. Color: yellow/green (RHS 145A and RHS 145C) with a little purple/violet (RHS N81B).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity.*—On the plant: about 4 to 6 months; lastingness of cut flowers: has not been observed.

*Fragrance.*—No fragrance.

Figure 2:
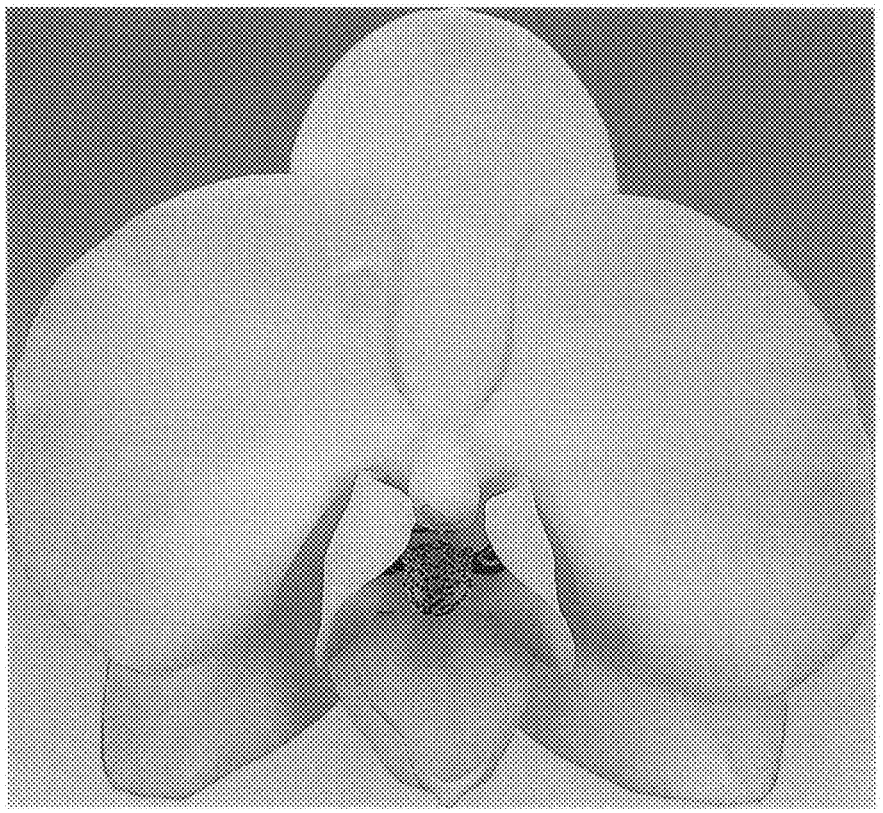
FIG. 2 shows a close-up view of the typical buds and flowers of 'Snow Virgin'.
Figure 3:
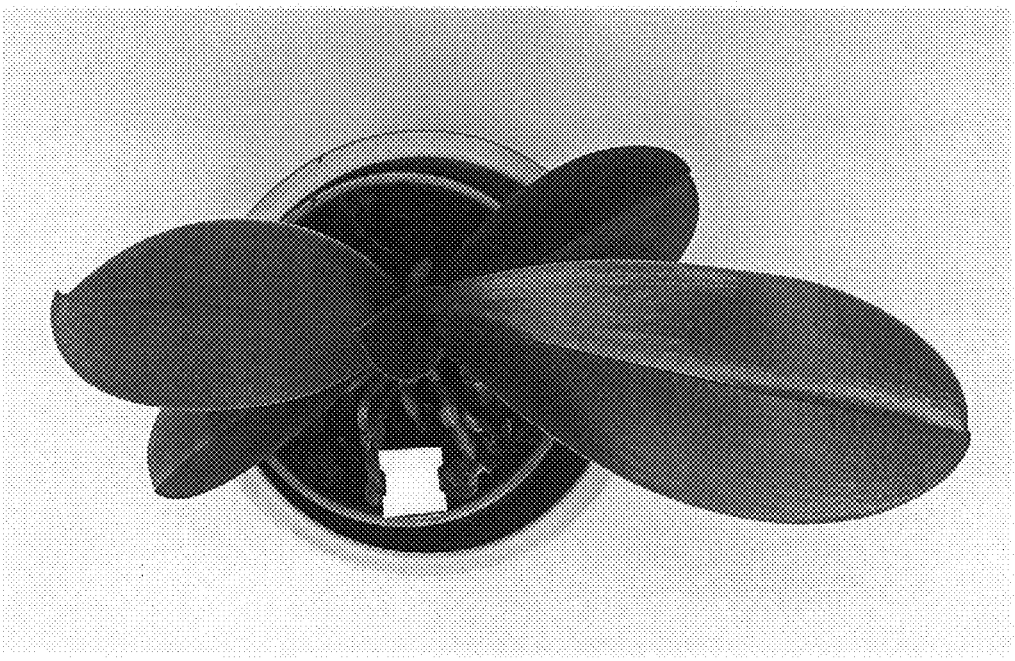
FIG. 3 shows a close-up view of the typical leaves of 'Snow Virgin'.

*Flower.*—Rate of opening: Flowers fully opened about 2 to 3 days after petal and sepal separation. Orientation at opening: slanted upward and outward. Shape: Typical shape of *Phalaenopsis*; see FIG. 2. Size (of single bloom): Height: about 8 cm. Diameter: about 8 cm. Depth of tube: about 15 mm.

*Petals.*—Quantity and arrangement: three petals and three sepals that are trimerous, overlapping and arranged in 2 whorls. Petals are more pronounced than sepals. Arrangement: Inner whorl comprises 3 petals: 2 lateral petals and labellum. 2 lateral petals: Overall shape: broadly ovate and weakly cupped. Apex: oval with a little notch. Margin: entire and weakly undulate. Base: broadly ovate. Length: about 60 mm. Width: about 45 mm. Texture: Upper surface: smooth and satiny. Under surface: smooth and satiny. Color (when fully opened): upper and under surface: white (RHS NN155C). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Apex: oval. Length: about 20 mm. Width (not flattened): about 23 mm. Texture: Upper and under surface: smooth and satiny. Color (when fully opened): Midlobe, upper surface: main color is white (RHS NN155C). From base upper edge is orange/red (RHS N34B) and on mid vein a small orange/red stripe (RHS N34A). At the base, on both sides of the midvein a purple/violet haze (RHS N81D). Both corners and in the center green/yellow (RHS 1B). Under surface: upper edges at the base are orange/red and the corners are yellow/green (RHS 150C). Main color is white (RHS NN155C). Lateral lobes, upper surface: main color is white (RHS NN155C). Lower edge is green/yellow (RHS 1B) and yellow (RHS 2B). From base some red/purple stripes (RHS 72A) and some greyed/orange stripes (RHS 164B). Under surface: main color is white (RHS NN155C). Lower edge is green/yellow (RHS 1B). From base upper edge red/purple (RHS 72B) and lower edge very thin orange/red (RHS N34B). Cirrhi: about 14 mm and wavy. Color: first white (RHS NN155C) then yellow (RHS 2C). Pestle (Callosities): Length: about 5 mm. Width (not flattened): about 8 mm. Color: white (RHS NN155C). Front is yellow (RHS 8C), top is yellow (RHS 8C and RHS 9A). Red/purple spots (RHS 59B).

*Sepals.*—Arrangement: Outer whorl comprises 3 sepals. Overall shape: elliptical and weakly cupped. Margin: entire and weakly undulate. Length: about 48 mm. Width: about 35 mm. Apex: oval; lateral little pointy. Texture: Upper and under surface: smooth and satiny. Color (when fully opened): Upper surface, dorsal and lateral: white (RHS NN155C). Under surface, dorsal and lateral: white (RHS NN155C) with a purple/violet haze (RHS N81C). Some lateral sepals also have a light yellow/green haze (RHS 145C).

*Pedicel.*—Length: about 40 mm. Diameter: about 4 mm. Texture: glabrous and smooth. Color: white (RHS NN155B) with a purple haze (RHS N78B) which runs into yellow/green (RHS 145B) and then into RHS 146C.

Reproductive organs:

*Arrangement.*—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column.*—Length: about 9 mm. Diameter: about 6 mm. Color: white (RHS NN155C).

*Pollinia.*—Quantity: two. Diameter: about 1 mm. Color: orange (RHS 24A).

*Ovary.*—Length: about 4 mm. Diameter: about 6 mm. Color: white (RHS NN155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Snow Virgin', as illustrated and described herein.

* * * * *